US00PP18033P3

(12) United States Plant Patent
Carruth

(10) Patent No.: US PP18,033 P3
(45) Date of Patent: Sep. 18, 2007

(54) CLIMBING ROSE PLANT NAMED 'WEKBECFOJ'

(50) Latin Name: *Rosa hybrida*
Varietal Denomination: WEKbecfoj

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 118 days.

(21) Appl. No.: 11/263,802

(22) Filed: Oct. 31, 2005

(65) Prior Publication Data

US 2007/0101467 P1 May 3, 2007

(51) Int. Cl.
*A01H 5/00* (2006.01)

(52) U.S. Cl. ..... Plt./109
(58) Field of Classification Search ..... Plt./109
See application file for complete search history.

*Primary Examiner*—Kent Bell

(57) ABSTRACT

A new variety of Climbing rose suitable for garden decoration, having flowers of irregularly striped and flecked pastel pink and yellow striped coloration.

1 Drawing Sheet

Classification: The present invention relates to a new *Rosa hybrida* plant.

Variety denomination: The new plant has the varietal denomination 'WEKbecfoj'.

BACKGROUND OF THE INVENTION

This invention relates to a new and distinct variety of Climbing Rose. It has as its seed parent the variety known as 'POUlclimb' (U.S. Plant Pat. No. 10,639) and as its pollen parent the variety known as 'WEKroalt' (U.S. Plant Pat. No. 11,518).

SUMMARY OF THE INVENTION

Among the features which distinguish the new variety from other presently available and commercial rose cultivars known to the inventor are the following combination of characteristics: its entirely smooth peduncle, its stipules margins lined with many stipitate glands, its very low thorned major stems, branches and new shoots and its large clusters of irregularly striped and flecked pastel pink and yellow striped flowers. The plant has a spreading climbing growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKbecfoj' may be asexually propagated by cuttings, budding and grafting. The budding and grafting successfully occurred on the plant/rootstock *Rosa hybrida* cv. 'Dr. Huey'.

Comparison with Parents

The new rose may be distinguished from its seed parent, 'POUlclimb' by the following combination of characteristics: whereas 'WEKbecfoj' bears single flowers (about 5 to 7 petals), 'POUlclimb' bears semi-double flowers with significantly heavier petalage (about 10 to 15 petals). The new variety has greenish yellow styles, whereas the seed parent has bright red styles. 'WEKbecfoj' bears its flowers on medium to long stems (about 23 to about 72 cm.), whereas 'POUlclimb' bears its flowers on significantly shorter medium length stems (about 18 to about 30 cms.).

The new variety may be distinguished from its pollen parent, 'WEKroalt' by the following combination of characteristics: whereas 'WEKbecfoj' bears single flowers (about 5 to 7 petals) of irregularly striped and flecked pastel pink and yellow striped coloration, 'WEKroalt' bears single to semi-double flowers with significantly heavier petalage (about 8 to 12 petals) of irregular striped and flecked red and white coloration. The new variety bears very few large prickles and no small prickles on its major stems, branches and new shoots, whereas the pollen parent bears several large and few small prickles on its major stems, branches and new shoots.

Comparison with the Closest Commercially Available Cultivar

The closest commercially available cultivar to the new variety is the seed parent 'POUlclimb'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of October. Phenotypic expression may vary with environmental, cultural and climatic conditions, as well as differences in conditions of light and soil.

FLOWER

The new variety usually bears its flowers in clusters of four to ten or more per stem. Flowers are borne in regular rounded clusters on medium to long stems (about 23 to about 72 cm.). Outdoors, the plant blooms abundantly and nearly continuously during the growing season. The flowers have a very slight tea fragrance.

BUD

The peduncle is about 2.7 to about 4.8 cm. in length, of slender caliper (about 0.15 to about 0.3 cm. in diameter), and usually erect. It is entirely smooth with some hairs. Peduncle color is between 144A and 143C sometimes very lightly suffused, especially on the side exposed to the sun, with between 187C and 183C.

Before the calyx breaks, the bud is about 0.8 to about 1.6 cm. in diameter at the widest point, about 1.4 to about 2.4 cm. in length, and very pointed in shape. The surface of the bud bears few foliaceous appendages sometimes with very few stipitate glands and hairs, usually with slender entire foliaceous parts extending beyond the tip of the bud about ½ or more of its length. Bud color is between 146A and 143A sometimes lightly suffused, especially on the side exposed to the sun, with between 187C and 183C.

The sepals are about 2.2 to about 3.6 cm. in length and about 0.6 to about 1.1 cm. in width at the widest point. The outer surface color of the sepal is between 146A and 143A sometimes lightly suffused, especially on the side exposed to the sun, with between 187C and 183C. The inner surface color of the sepal is between 137A and 138B and covered with fine wooly tomentum; sepal margins are lined with few stipitate glands and hairs.

The receptacle of the flower is of medium length (about 0.5 to about 0.9 cm.) and average in caliper (about 0.6 to about 0.9 cm. in diameter). The receptacle is globular to almost rounded in form. Its surface is very smooth with very few hairs and stipitate glands and with thick fleshy walls. The receptacle color is between 144A and 141C.

As the petals open (after the calyx breaks), the bud is about 1.3 to about 2.1 cm. in diameter at the widest point, about 2.2 to about 3.6 cm. in length, and pointed to moderately ovoid in form. The color of the under surfaces of the newly opened petals is between 12B and 18C suffused toward the petal edge with as dark as between 53A and 60A and sometimes irregularly striped and flecked with as light as between 4C and 1D. There is no visible change in coloration at the point where the petal attaches on the under surface. The color of the upper surfaces of the newly opened petals is irregularly striped and flecked with as dark as between 50A and 54D to as light as between 4C and 8D. At the point where the petal attaches, there is a very large zone of between 12B and 9B.

BLOOM

When fully open, the bloom ranges from about 7.0 to about 9.6 cm. in diameter. Petalage is single with about 5 to 7 petals and about 0 to 2 petaloids irregularly arranged. When partially open, the bloom form is very cupped and the petals are loosely cupped to moderately undulated with petal edges moderately reflexed outward. When fully open, the bloom form is somewhat cupped to almost flat and the petals are loosely cupped to almost flat to moderately undulated with petal edges moderately reflexed outward.

PETALS

The substance of the petals is moderately slight and of somewhat thin thickness, with upper surfaces moderately satiny and under surfaces slightly shiny to almost matte. The petals are about 4.0 to about 4.8 cm. in length and about 3.7 to about 5.3 cm. in width at the widest point. Petal margins are entire to sometime broadly crenate.

The outer and inner petals are broadly obovate to almost round in shape with rounded apices.

Petaloids are about 1.8 to about 4.0 cm. in length and about 0.8 to about 4.0 cm. in width at the widest point. Petaloids are irregularly shaped somewhat obovate to oblanceolate with rounded apices.

NEWLY OPENED FLOWER

The under surface color of the outer and inner petals is between 6D and 18C suffused toward the petal edge with as dark as between 61B and 61D and sometimes irregularly striped and flecked with as light as between 4C and 155B. The under surface is sometimes moderately blushed with near 61A. There is no visible change in coloration at the point where the petal attaches on the under surface.

The upper surface color of the outer and inner petals is irregularly striped and flecked with as dark as between 58B and 61D to as light as between 4D and 157C. At the point where the petal attaches, there is a moderately large zone of near 12B. That attachment zone is surrounded by a broader zone of between 5D and 2C in color.

The under and upper surface color of the petaloids are similar in coloration to the upper and under surfaces of the outer and inner petals.

The general tonality of the newly opened flower is irregularly striped and flecked with as dark as between 57D and 61D to as light as between 4D and 157C.

THREE-DAY-OLD FLOWER

The under surface color of the outer and inner petals is between 4D and 155D suffused toward the petal edge with as dark as between 61C and 55B and sometimes irregularly striped and flecked with as light as between 4D and 155D. The under surface is sometimes moderately blushed with near 61A. There is no visible change in coloration at the point where the petal attaches on the under surface. The upper surface color of the outer and inner petals is irregularly striped and flecked with as dark as between 58C and 55B to as light as between 155A and 155D. At the very tip of the petal, there is a somewhat small zone of between 12C and 9C. That attachment zone is surrounded by a broader zone of between 155A and 157C in color.

The under and upper surface color of the petaloids are similar in coloration to the upper and under surfaces of the outer and inner petals.

The general tonality of the three-day-old flower is irregularly striped and flecked with as dark as between 58C and 65B to as light as between 155A and 155D.

On the spent bloom, the petals usually drop off cleanly.

In October in Upland, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 110) and are arranged regularly about the pistils; a few are mixed with petaloids. The filaments are of medium length (about 0.4 to about 1.1 cm.) most with anthers. Filaments are between 13B and 12B in color sometimes lightly suffused with near 33A. The anthers are moderately large for the class and all open approximately at the same time. Anther color is between 16A and 16B when immature and between 200A and 163C at maturity. Pollen is abundant and between 20B and 22B in color.

FEMALE REPRODUCTIVE ORGANS

Pistils vary in number (average about 45). The styles are moderately even, average in length (about 0.4 to about 0.9 cm.), average in caliper and moderately loosely bunched. Stigma color is between 12C and 9C. Style color is between 4D and 149D sometimes very lightly suffused with near 53C. Ovaries are usually all enclosed in the calyx.

Hips are of average length (about 1.5 to about 2.1 cm.), globular to almost rounded in form, and between 28A and 30B in color when ripe. The hip surface is very smooth with thick fleshy walls. The sepals are moderately permanent and usually straight in shape.

The seeds are irregularly rounded, smooth in texture, approximately 8 to about 15 per hip, about 0.4 to about 0.6 cm. in diameter at the widest point and between 164D and 165D in color.

FOLIAGE

The compound leaves are usually comprised of three to seven leaflets and are borne abundantly. The five-leaflet leaves are about 6.4 to about 13.1 cm. in length and about 6.0 to about 10.6 cm. in width at the widest point, moderately leathery to somewhat crisp in texture and glossy in finish. The terminal leaflets are about 2.8 to about 7.0 cm. in length and about 2.5 to about 4.1 cm. in width at the widest point, shaped moderately ovate to somewhat oval with acute apices and rounded to somewhat acute bases. Their margins are usually simply serrate.

The upper surface color of the mature leaf is between 147A and 139A. The under surface color of the mature leaf is between 147B and 139B. The upper surface color of the young leaf is between 137B and 143B, sometimes moderately suffused mostly on the very edge of the leaf with between 187A and 183B. The under surface color of the young leaf is between 146B and 146C, sometimes lightly suffused with between 187B and 183B.

The rachis is average in caliper and rough. The upper side is shallowly grooved with few hairs and some stipitate glands on the edges of the grooves. The under side of the rachis is rough with few small prickles. The rachis color is between 144A and 137C sometime moderately suffused with between 183B and 187B.

The stipules are about 0.9 to about 1.5 cm. in length and moderately wide (about 0.5 to about 0.7 cm.) with long straight points that usually turn out at an angle of more than 45 degrees and often recurve toward the stem. Stipules margins are lined with many stipitate glands. The stipules color is between 144A and 137B sometime lightly suffused, especially on the new shoots with between 183B and 187C.

The petiole is average in caliper and rough. The upper side is shallowly grooved with few hairs and some stipitate glands on the edges of the grooves. The under side of the petiole is rough with few small prickles. The petiole is about 0.8 to about 1.7 cm. in length and about 0.1 to about 0.2 cm in diameter at the widest point. The petiole color is between 144A and 137C sometime moderately suffused with between 183B and 187B.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a spreading climbing growing habit with canes about 250 to about 380 cm. in length with full branching. It displays very vigorous growth and the canes are of medium caliper for the class.

The color of the major stems is between 146C and 152D. They bear few large prickles that are about 0.7 to about 1.0 cm. in length. The large prickles are moderately hooked downward with a somewhat short narrow oval base; prickle color is between 165A and 199A. The major stem bears no small prickles.

The color of the branches is between 146C and 137B. They bear few large prickles which are of similar size and shape to the large prickles on the major stems; prickle color is between 164A and 165B. The branches bear no small prickles.

The color of the new shoots is between 144A and 137C sometimes lightly suffused with between 187B and 183B. They bear few large prickles which are of similar size and shape to the large prickles on the major stems; prickle color is near 145B usually moderately suffused with between 187B and 183B. The shoots bear no small prickles.

I claim:

1. A new and distinct Climbing rose plant of the variety substantially as described and illustrated herein.

* * * * *

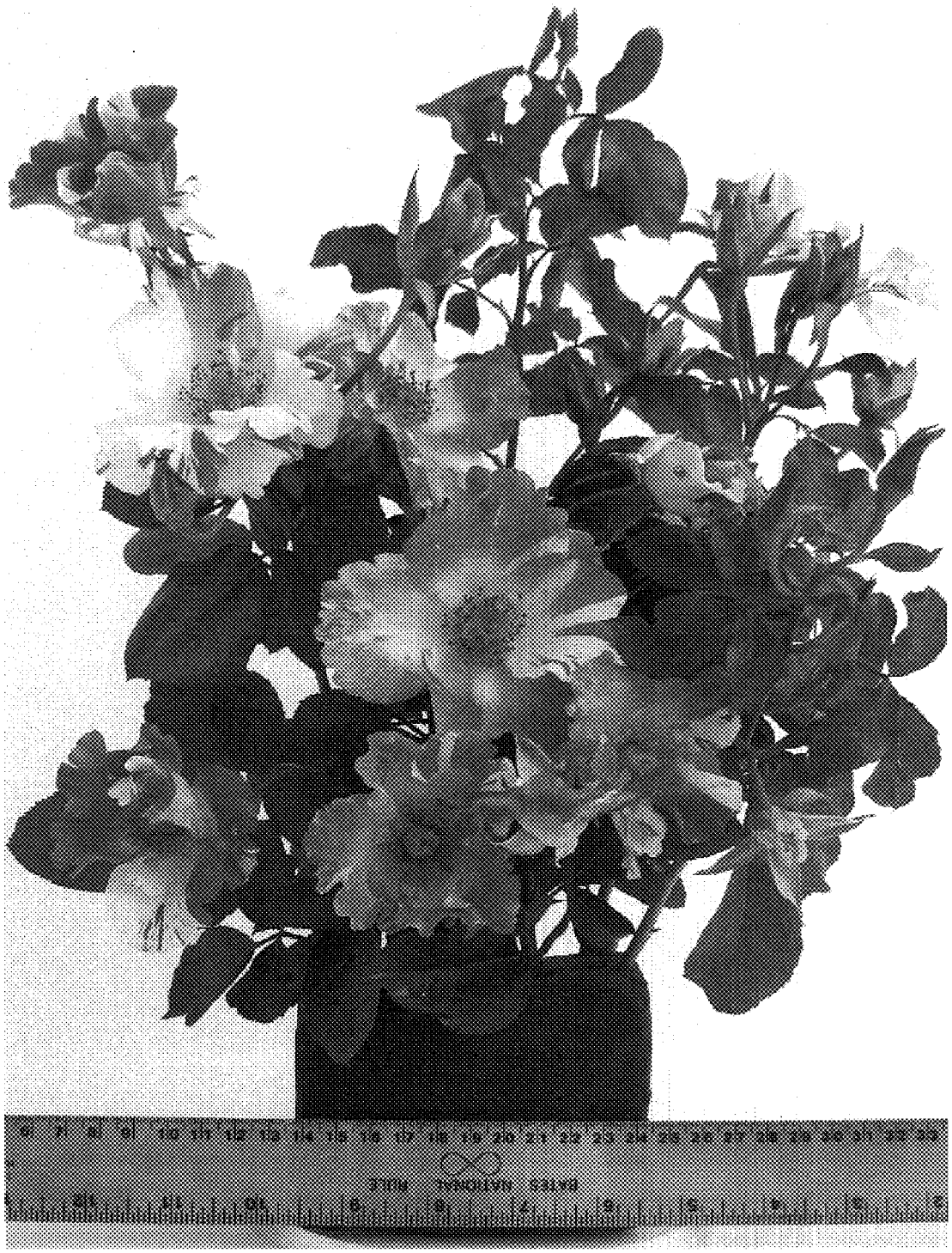
FIG. 1 INGOLVIN SAYO